(12) United States Patent
Boudoux et al.

(10) Patent No.: US 8,792,757 B2
(45) Date of Patent: Jul. 29, 2014

(54) DOUBLE CLAD FIBER COUPLER AND DEVICE

(75) Inventors: Caroline Boudoux, Montreal (CA); Nicolas Godbout, Verdun (CA); Simon Lemire-Renaud, Montreal (CA)

(73) Assignee: Polyvalor, Limited Partnership, Montreal, Quebec (CA)

( * ) Notice: Subject to any disclaimer, the term of this patent is extended or adjusted under 35 U.S.C. 154(b) by 278 days.

(21) Appl. No.: 13/356,970

(22) Filed: Jan. 24, 2012

(65) Prior Publication Data
US 2012/0190928 A1 Jul. 26, 2012

Related U.S. Application Data

(60) Provisional application No. 61/435,485, filed on Jan. 24, 2011.

(51) Int. Cl.
G02B 6/26 (2006.01)
G02B 6/28 (2006.01)
A61B 1/00 (2006.01)
A61B 5/00 (2006.01)

(52) U.S. Cl.
CPC .............. *A61B 1/0017* (2013.01); *A61B 5/0068* (2013.01); *A61B 5/0084* (2013.01); *G02B 6/2821* (2013.01)
USPC ................................ 385/43; 385/42; 600/182

(58) Field of Classification Search
None
See application file for complete search history.

(56) References Cited

U.S. PATENT DOCUMENTS

| 2001/0017962 A1* | 8/2001 | Kim et al. ................. 385/43 |
| 2008/0205833 A1* | 8/2008 | Fu et al. .................. 385/117 |
| 2011/0226940 A1* | 9/2011 | Yun ...................... 250/227.11 |
| 2011/0273764 A1* | 11/2011 | Goldberg ................ 359/341.3 |

FOREIGN PATENT DOCUMENTS

| JP | 4-56907 A | * | 2/1992 |
| JP | 2004-165350 A | * | 6/2004 |
| WO | WO 2009/155536 A2 | * | 12/2009 |

OTHER PUBLICATIONS

S. Lemire-Renaud et al. Double-clad fiber coupler for endoscopy. Optics Express, 18:10:9755-9764, May 2010.*
S. Ryu et al. Combined system of optical coherence tomography and fluorescence spectroscopy based on double-cladding fiber. Optics Letters, 33:20:2347-2349, Oct. 2008.*

* cited by examiner

*Primary Examiner* — Mike Stahl

(57) ABSTRACT

There is described a double-clad fiber coupler (DCFC) composed of two double-clad fibers that have been fused together and tapered. The DCFC allows the propagation of light in the fundamental mode in its single-mode core with very little loss. Back reflected light may be collected two ways: by the core of the double-clad fiber and by the inner cladding of the double-clad fiber.

19 Claims, 12 Drawing Sheets

DOUBLE CLAD FIBER COUPLER AND DEVICE

CROSS-REFERENCE TO RELATED APPLICATIONS

The present application claims priority under 35 USC 119 (e) of U.S. Provisional Patent Application No. 61/435,485, filed on Jan. 24, 2011, the contents of which are hereby incorporated by reference.

TECHNICAL FIELD

The present invention relates to the field of double clad fiber couplers for medical fields such as endoscopy and confocal endomicroscopy.

BACKGROUND OF THE ART

Endoscopy procedures allow clinicians to visualize internal organs in a much less invasive manner than exploratory surgeries. The use of optical fibers reduces the size and increases the flexibility of endoscopes, thus potentially allowing safer, faster and cheaper office-based procedures. Advances in endoscopy, such as imaging with coherent fiber bundles, have also paved the way towards endomicroscopy, which is an imaging technique combining the flexibility of endoscopy with the advantages of confocal microscopy, namely micrometric resolution and optical sectioning.

Reflectance single fiber endoscopy is however subject to speckle noise as the use of lasers and single-mode (SM) fibers results in imaging that is both temporally and spatially coherent. The use of a double-clad fiber (DCF) dramatically reduces speckle contrast while improving signal collection. In order to preserve lateral resolution, the SM core of the DCF is used for illumination, while the multi-mode (MM) inner cladding is used for collection of partially incoherent light reflected from the sample. Coupling light in and out of a DCF is typically performed using a free space beam splitter setup resulting in a greater than 6 dB loss of the weak SM signal and a greater than 3 dB loss in the MM signal, making the system quite vulnerable to misalignment due to mechanical motions.

Therefore, despite the advances made, coupling remains an issue for the use of DCF in medical imaging techniques.

SUMMARY

There is described herein a double-clad fiber coupler (DCFC) composed of two double-clad fibers that have been fused together and tapered. The DCFC allows the propagation of light in the fundamental mode in its single-mode core with very little loss. Back reflected light may be collected two ways: by the core of the double-clad fiber and by the inner cladding of the double-clad fiber.

In some embodiments, the DCFC is used for single fiber endoscopy by separating SM signals from MM signals to combine low-speckle reflectance maps with interferometric depth profiles to obtain 3D reconstructions and thus emulate stereoscopic vision. For this application, the DCFC may be used as is or with a taper at an imaging end. The taper may have an inner cladding to core mode ratio of about 6.0 or greater. In other embodiments, the DCFC is used for confocal endomicroscopy, by setting the ratio between the inner cladding and the core mode to less than or equal to 6.0.

In accordance with a first broad aspect, there is provided a double-clad fiber coupler comprising a first double-clad fiber having a first end, a second end, and a first middle portion therebetween, and having a first core, a first inner cladding, and a first outer cladding; a second double-clad fiber having a third end, a fourth end, and a second middle portion therebetween and having a second core, a second inner cladding, and a second outer cladding; and a fused region composed of the first middle portion fused to the second middle portion, wherein the first core and the second core remain separate and the first inner cladding and the second inner cladding are coupled to form a fused inner cladding, the fused region comprising a first diameter transition section, a constant diameter section, and a second diameter transition section, the first diameter transition section corresponding to a down-taper of the fused region and the second diameter transition section corresponding to an up-taper of the fused region, the fused region section having a predetermined taper ratio, and wherein the fused region allows light injected in the first core at the first end to be transmitted in the first core to the second end, light injected in the first core at the second end is transmitted in the first core to the first end, and light injected in the first inner cladding at the second end is substantially equally split between the first inner cladding towards the first end and the second inner cladding towards the third end.

In accordance with another broad aspect, the double-clad fiber coupler is provided a double-clad fiber imaging system. The system comprises a laser source for generating a light signal; a single mode fiber operatively connected to an output of the laser source for receiving and propagating the light signal; an imaging module operatively connected to the second end of the double-clad fiber coupler and adapted for sampling coherent light propagating from the first end of the double-clad fiber coupler to the second end; a first photodetector operatively connected to the third end of the double-clad fiber coupler for collecting backscattered diffuse light from the second end of the double-clad fiber coupler to the third end; and a second photo-detection operatively connected to the first end of the double clad fiber coupler for collecting backscattered coherent light from a core of the second end of the double-clad fiber coupler to the first end.

The imaging system may be adapted for wide-field endoscopy, for confocal endomicroscopy, and for other applications, as will be described in more detail below. The double-clad fiber coupler may be provided with or without a tapered second end with a given inner cladding/core mode diameter ratio, depending on the application.

In some embodiments, the fused region of the double-clad fiber coupler allows at least 90% of the light injected in the first core at the first end to be transmitted in the first core to the second end, at least 90% of the light injected in the first core at the second end to be transmitted in the first core to the first end, and light injected in the first inner cladding at the second end is substantially equally split between the first inner cladding towards the first end and the second inner cladding towards the third end, with at least 40% transmission in each end.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
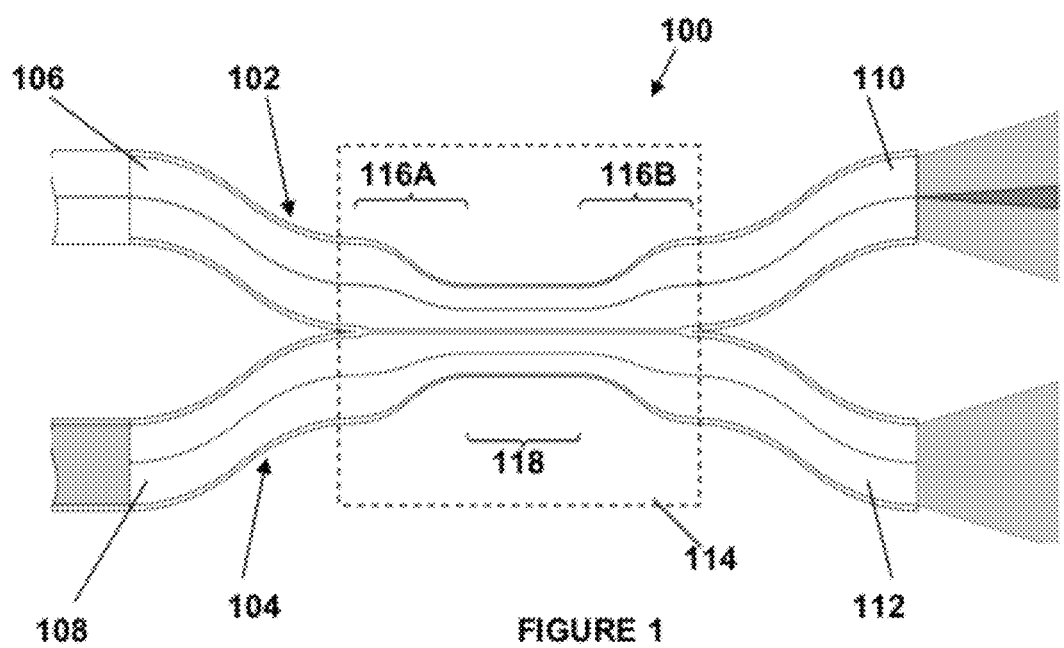
FIG. 1 is a schematic illustration of a double-clad fiber coupler in accordance with one embodiment.

FIG. 1 illustrates an exemplary Double-Clad Fiber Coupler (DCFC) 100. In this embodiment, the DCFC 100 was made by fusing and tapering two commercially available DCF segments 102, 104. Each segment 102, 104, has an inner cladding, an outer cladding, and a core. The first DCF segment 102 acts as a first branch and is defined by a first end 106, a second end 110, and a middle portion therebetween. The second DCF segment 104 acts as a second branch and is defined by a third end 108, a fourth end 112, and a middle portion therebetween. A fused region 114 is composed of the middle portion of DCF segment 102 fused to the middle portion of DCF segment 104. In the fused region 114, the cores of segments 102, 104 remain separate and while the inner claddings are coupled to form a fused inner cladding. The fused region 114 comprises a first diameter transition section 116a, a constant diameter section 118, and a second diameter transition section 116b. The first diameter transition section 116a is a down-taper of the fused region 114 and the second diameter transition section 116b is an up-taper of the fused region 114. The fused region 114 has a predetermined taper ratio. The predetermined taper ration may vary between about 0.1 and about 0.6, and in the embodiment illustrated it has been set to 0.3.

In the embodiment illustrated, each DCF segment 102, 104 has a 9 µm diameter core, a pure silica inner cladding of 105 µm in diameter and a fluorine-doped outer cladding of lower refractive index of 125 µm in diameter. The core numerical aperture (NA) is 0.12 while the inner cladding NA is 0.20. The diameter of the core may vary between about 3.0 µm and 10.0 µm, +/−20%. The diameter of the outer cladding may vary between about 80 µm and about 200 µm, +/−20%. The diameter of the inner cladding may also vary. It may be as large as possible while allowing enough spacing with the outer cladding to guide light substantially losslessly. For example, the spacing may be about 10.0 µm or greater while being limited by the diameter of the outer cladding.

The DCF segments 102, 104 may be identical or may have slight differences in terms of dimensions, composition, and light propagating properties. Some exemplary materials for the DCF segments 102, 104 are various polymer and glass types, such as silica (pure or doped).

When created from commercially available DCF segments, the DCFC 100 may be obtained using a computer-controlled fusion and tapering setup. In one embodiment, this setup consists of a traveling oxygen-propane micro-torch on a three-axis motorized stage and of two linear stages for stretching. Other setups may also be used. Alternatively, various fabrication techniques may be used to create the DCFC 100 without starting from commercially available DCF segments.

In one embodiment, the fabrication process begins by stripping the middle portions of the DCF segments 102, 104 from their polymer coating and cleaning them with acetone. The middle portions of the DCF segments 102, 104 are pressed together by holding clamps containing V-shaped grooves and inspected with a microscope mounted over the setup. For on-line characterization of the core mode transmission, DCF segment 102 is spliced with a single-mode fiber (SMF) on both ends 106, 110 and connected respectively to a broadband source and to an optical spectrum analyzer. The two segments 102, 104 are fused side-by-side with a micro-torch traveling over 4-8 mm along the fibers for approximately 2 minutes. The fused region 114 is then stretched, at a slightly lower flame temperature, at a stretching rate of 0.1 mm/s, with the micro-torch traveling back-and-forth along a constant 8 mm length. This heating length ensures transition slopes mild enough for an adiabatic (lossless) transition of the core mode. The tapering process is stopped when a target of 15 dB coupling ratio from the first end 106 to the fourth end 112 is reached. The reduction factor 0.3 of the constant region 118 is deduced from a total elongation of 20 mm. The device is packaged on a quartz substrate while still under tension on the setup and then inserted in a stainless steel tube. The inner cladding mode transmission is characterized post-fabrication. Losses in the fundamental core mode are minimized through an adiabatic transition from the full-diameter fused section to the reduced constant section 118 of the DCFC 100. As the constant section 118 has a moderate reduction factor of 0.3, coupling between the fundamental modes of each segment 102, 104 is negligible.

Coupling of the inner cladding modes may be explained using geometrical optics. In the down-taper section 116a, as the cross-section of the coupler 100 diminishes, the propagation angle of each ray increases. Most rays are guided by the outer cladding of the new waveguide consisting of the two fused DCFs 102, 104. In the up-taper section 116b, rays having a propagation angle smaller than the critical angle resume propagation in the inner cladding. Rays essentially distribute uniformly across the coupler cross-section, resulting in an approximate 50:50 transmission. The high number of modes propagating in the inner cladding favors achromaticity and power equipartition.

Figure 2:
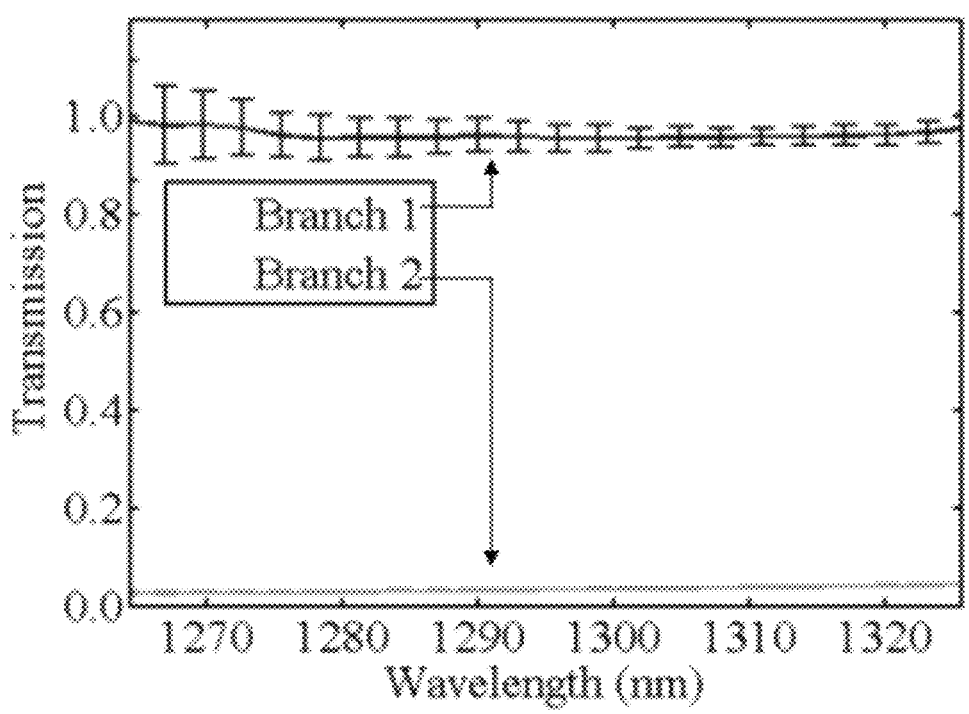
FIG. 2 is a graph of an exemplary spectral response of single-mode signal transmission for each branch of the coupler of FIG. 1.

Core signal transmission of the exemplary DCFC 100 may be monitored during fabrication with a conventional broadband source and an optical spectrum analyzer. FIG. 2 shows core mode signal transmission in each branch of the coupler. The average isolation between the cores of the two branches is 15 dB and transmission in branch 1 is >95% across the illumination spectrum (1265-1325 nm).

Figure 3:
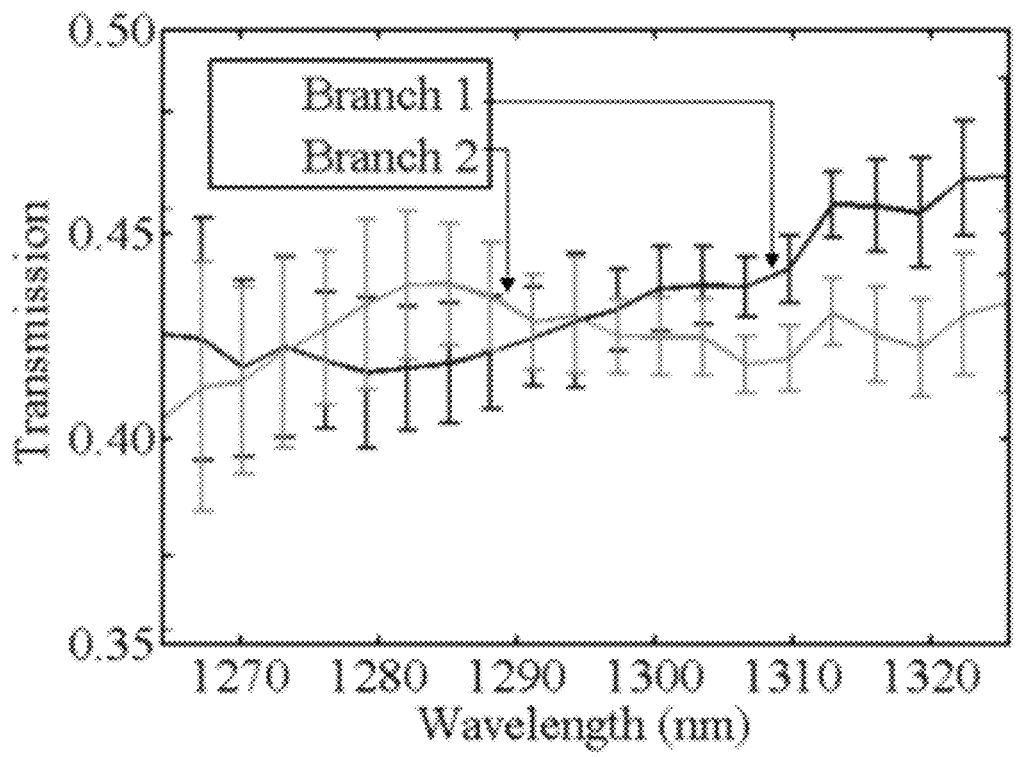
FIG. 3 is a graph of an exemplary spectral response of the multi-mode signal transmission for each branch of the coupler of FIG. 1.

Inner cladding signal characterization requires more attention. In order to have repeatable results, care must be taken to excite equally each mode guided by the inner cladding. This can be done by using a low spatial coherence source like a halogen lamp or a diffused wavelength swept laser source. FIG. 3 shows the transmission of the inner cladding signal in each branch of the coupler. Inner cladding transmission in each branch of this exemplary DCFC 100 ranges between 40-46% over the illumination spectrum. The exemplary achromatic DCFC 100 has a core transmission of >95% and an average transmission >42% for the inner cladding modes. In addition to the increased collection power through the inner cladding of coupler 100, the use of the exemplary DCFC 100 allows a 6 dB gain over the free space beam splitter approach for the core signal, in addition to being much more robust against misalignments and less sensitive to back reflections.

Figure 4:
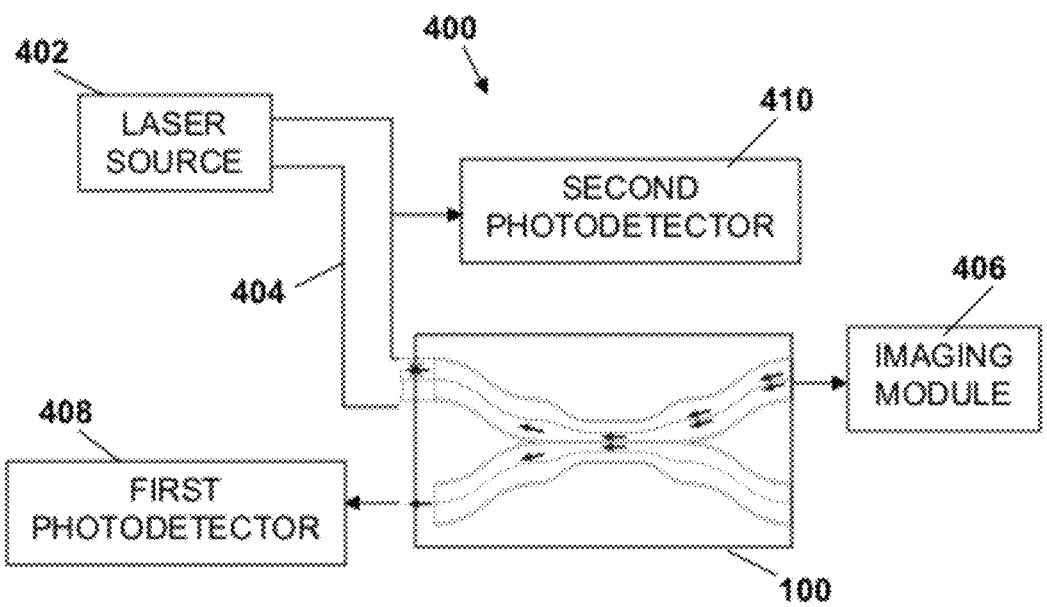
FIG. 4 is an exemplary double-clad fiber imaging system using the coupler of FIG. 1.

The DCFC 100 is compatible with many scanning techniques (MEMS, resonant micro-scanners and spectral encoding) and imaging modalities (reflectance, fluorescence). FIG. 4 illustrates an exemplary double-clad fiber imaging system. The DCFC 100 is coupled to a laser source 402 via a SMF 404. An imaging module 406 receives as input coherent light propagating from the first end 106 to the second end 110 of segment 102. Light backscattered by the sample and transmitted by the imaging module 406 to the second end 110 consists of a coherent (or singly backscattered) component and a diffuse (or multiply backscattered) component. The coherent portion is collected by the core of segment 102 while a portion of the diffuse component is collected by the inner cladding of segment 102. The DCFC 100 transmits most of the coherent light back in the original branch to the first end 106 while the diffuse component is propagated in the inner cladding and is equally split between both branches, towards the first end 106 and the third end 108. The diffuse component received at the third end 108 is collected by a first photo-detector 408. The coherent component received at the first end 106 is collected by a second photo-detector 410. Most of the diffuse component received at the first end 106 is filtered out by the SMF 404.

Figure 5:
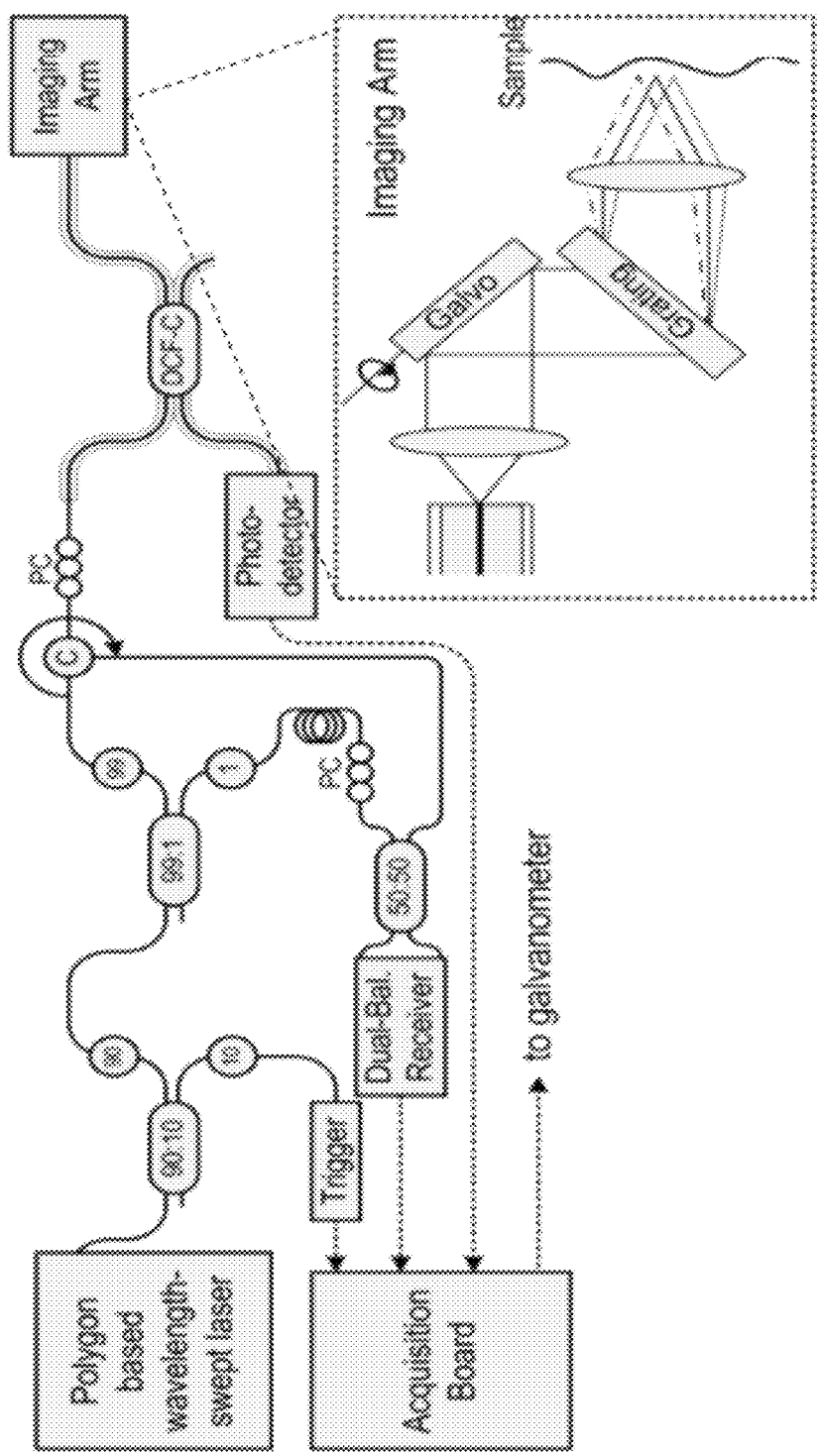
FIG. 5 is an exemplary setup used to test the coupler of FIG. 1 for wide-field spectrally encoded endoscopy.

In one embodiment, the imaging system is used for widefield endoscopy. FIG. 5 illustrates the set-up used to test the DCFC 100 for spectrally encoded endoscopy. Spectral encoding is a scanning technique in which broadband laser light is dispersed by a grating to perform a rapid 1D-scan of a sample by encoding spatial location with wavelength. Spectral detection allows rapid imaging of large field-of-views without the need for fast actuators within the probe and may include interferometric acquisition to extract sample depth. The second (or slow) scan axis may be performed mechanically with a micro-motor or by rotating the probe. This scanning technique can be applied to endoscopy, confocal microendoscopy as well as coherent anti-Stokes Raman spectroscopy (CARS) imaging in order to yield high resolution (>1000×1000 pixels) reflectance or fluorescence images. Alternatively, spectral encoding may be performed with a wavelength-swept laser and temporal detection to obtain high frame rate images and simpler detection schemes for fluorescence imaging.

The spectrally encoded endoscopy (SEE) setup of FIG. 5 couples wavelength scanning for rapid imaging, interferometric detection for depth assessment, and DCFC 100 for high throughput and low speckle imaging. Indeed, since the DCFC 100 is a null coupler for the SM channel and allows collection of 42% of the inner-cladding partially coherent light, it can be used to acquire simultaneously low-speckle images of the sample via the inner-cladding light and height profiles via SM interferometric detection. The entire setup is fiber-based which makes it insensitive to misalignments and back-reflections.

The laser source is a polygon-based rapid wavelength-swept laser centered at 1302 nm (−10 dB wavelength range: 1257 nm-1347 nm, instantaneous line width of 0.1 nm) and providing >25 mW of average output power at repetition rate of 9.8 kHz. Two achromatic fiber-based couplers (90%:10% and 99%:1%) are used to tap laser light for triggering purposes and interferometric measurement respectively. Triggering is performed with a grating-based filter (not shown) which selects a wavelength and generates an optical pulse at the beginning of the wavelength-swept spectrum. The 99:1 coupler separates light into a sample arm (99%) and a reference arm (1%) which is matched in length and in polarization state (through the drop-in polarization controller) with the sample arm. Light from the sample arm passes through a circulator and is coupled to the core of the DCFC through a simple fusion splice. As the SMF and the single mode core of the DCFC have similar mode field diameters, single mode transmission is achieved with negligible loss at the splice. Since there is negligible cross-talk between the cores of the two DCFs in the DCFC, >95% of the laser light is transmitted to the imaging arm consisting of a collimating lens, a galvanometer mounted mirror, a transmission grating and a focusing lens. A polarization controller was used to optimize transmission through the grating which was used in Littrow configuration for increased diffraction efficiency in the first order.

Part of the diffuse component is sent to an InGaAs photo-detector and digitized using a high acquisition rate analog-to-digital converter (A/D) board to produce a low-speckle reflectance map. At the splice between the DCFC and the SM fiber, the other part of the diffuse component diffracts in the cladding and is ultimately absorbed by the polymer coating. Through a fiber circulator, SM light from the sample is recombined with the reference arm using an achromatic 50:50 coupler and is detected with a dual balanced InGaAs photo-detector to extract fringe data without the DC component. The detection arm includes a variable delay line (not shown in FIG. 5) to accommodate different imaging arm lengths. Signals from the dual-balanced detector are digitized using a second input of the acquisition board at 180 MHz.

Figure 6:
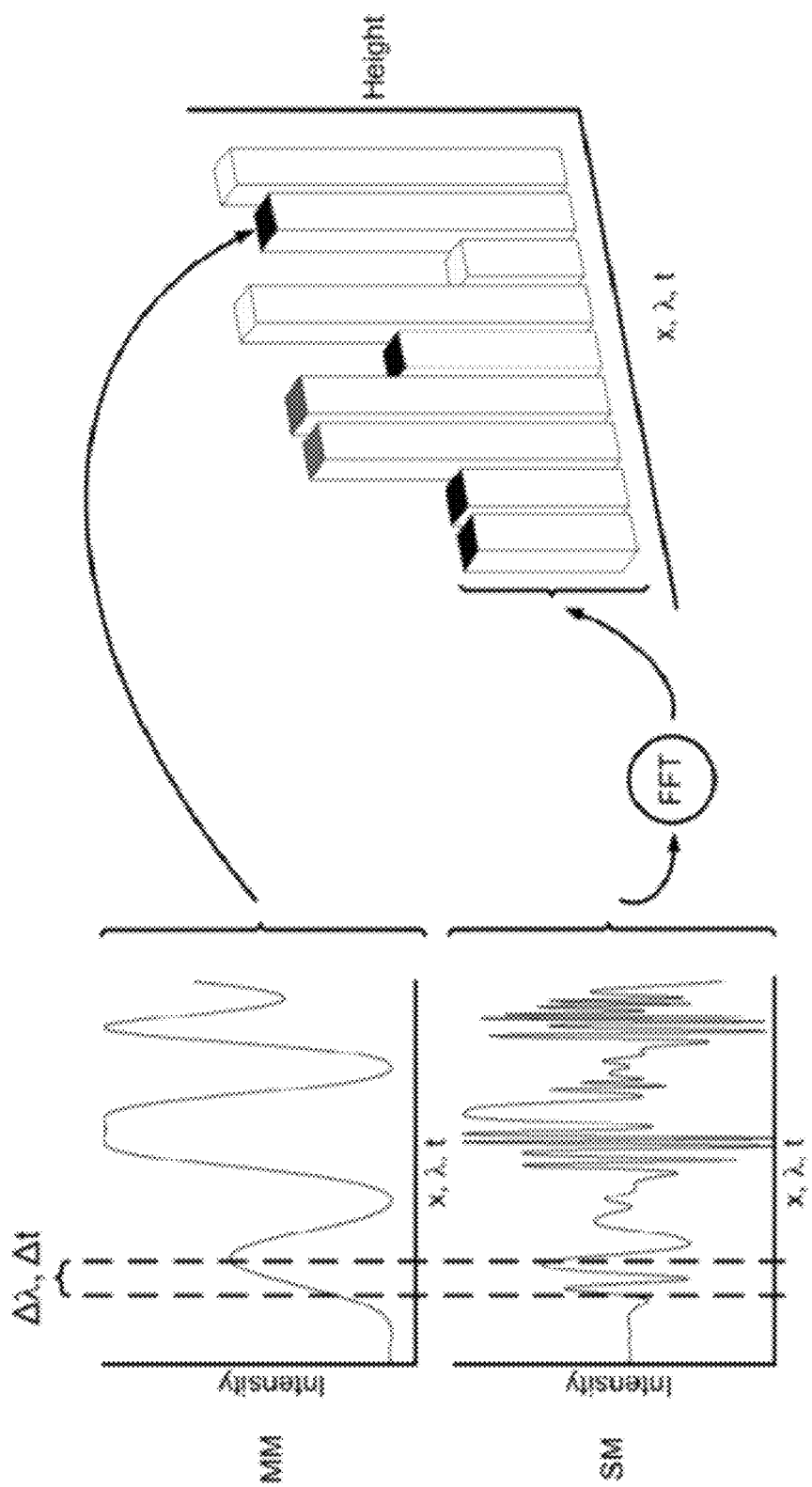
FIG. 6 illustrates an exemplary 3D imaging processing from superposition of multi-mode and single-mode data using the setup of FIG. 5.

FIG. 6 shows simulated signals acquired from the MM and SM fibers using a wavelength-swept SEE approach. MM data provides low-speckle, high intensity reflectance profiles while SM data from a Mach-Zehnder interferometer provides depth information. This depth information is extracted from the frequency of the interferogram which results from the slight wavelength sweep ($\Delta\lambda$) occurring during the pixel dwell time ($\Delta t$). Neglecting dispersion over $\Delta\lambda$, and considering that the sample's height is constant over a pixel, the frequency of the interferogram is proportional to the optical path difference, itself proportional to the height of the sample. The frequency of the interferogram is retrieved by Fourier transforming SM data over ($\Delta t$), which is digitized at an acquisition rate 36 times higher than the reflectivity MM data. This technique is a low bandwidth equivalent of optical frequency domain imaging (also referred to as swept-source optical coherence tomography) and can only detect the height of one interface, as opposed to other interferometric techniques such as optical coherence tomography detecting multiple interfaces inside a sample. To compensate for the low intensity regions (for example destructive speckle interference present in the single-mode data) the height reconstruction is filtered using a median filter. Final images emulating stereoscopic vision are obtained by mapping the low-speckle MM reflectance data on the 3D profile of the sample.

Image acquisition, processing and display is performed through an exemplary platform which acquires 384 lines of 384 pixels per image (at a line rate of 9.85 kHz, corresponding to the laser sweep rate) resulting in an image acquisition rate of 25.5 frames per second. Height reconstruction was post-processed and it took ~45 seconds with the exemplary post-processing algorithm to reconstruct each height profile with a standard computer. In another embodiment, a fast FFT algorithm in C++, with a computer capable of performing more than 1 million 64-point FFT per second could retrieve a few 3D profiles each second, while displaying processing-free reflectance images at video rate.

FIGS. 7a-7d show a spectrally encoded image of a rough plastic figurine (FIG. 7d) acquired with DCFC 100 and the table top imaging system described in FIG. 5. The speckle contrast diminution using a DCF fiber can be clearly seen by comparing FIG. 7a—obtained with the SM channel for illumination and detection at circulator output—and FIG. 7b—obtained with the MM detection channel. Speckle contrast was characterized using a highly diffusive abrasive paper (1 micron grit, images not shown) and calculated as the standard deviation of a region of interest over its mean. Speckle contrasts for SM and MM collection paths were 0.8±0.1 and 0.16±0.03 respectively, resulting in a diminution of speckle contrast of a factor 5. Theoretically, a fully developed speckle pattern yields a speckle contrast of 1 and drops as $C=1/\sqrt{N}$ where N is the number of independent speckle patterns or propagation modes. Assuming that the reflected light on the sample conserves its linear polarization, the number of modes propagating through the inner cladding is $N \approx 8(aNA/\lambda)^2$ where a is the radius of the inner cladding, $\lambda$ is the instantaneous wavelength and NA is the numerical aperture of the fiber, which corresponds to ~520 modes. Assuming a fully developed speckle contrast for the perfectly coherent image, the multimode speckle contrast should drop to 0.04. The discrepancy between theoretical and experimental values may arise from the sample (e.g. not allowing fully developed speckle patterns), the coupler (e.g. the energy of each mode not being equally distributed over each branch), and/or the aperture (e.g. providing a limited sampling a non-uniform modal density).

The hypothesis that higher order modes are not excited or are attenuated is also supported by the fact that, while we observe a 3 to 9 fold increase (depending on sample type) in signal from the inner cladding with respect to the core, this increase is not commensurate to the increase in number of modes.

Figure 7:
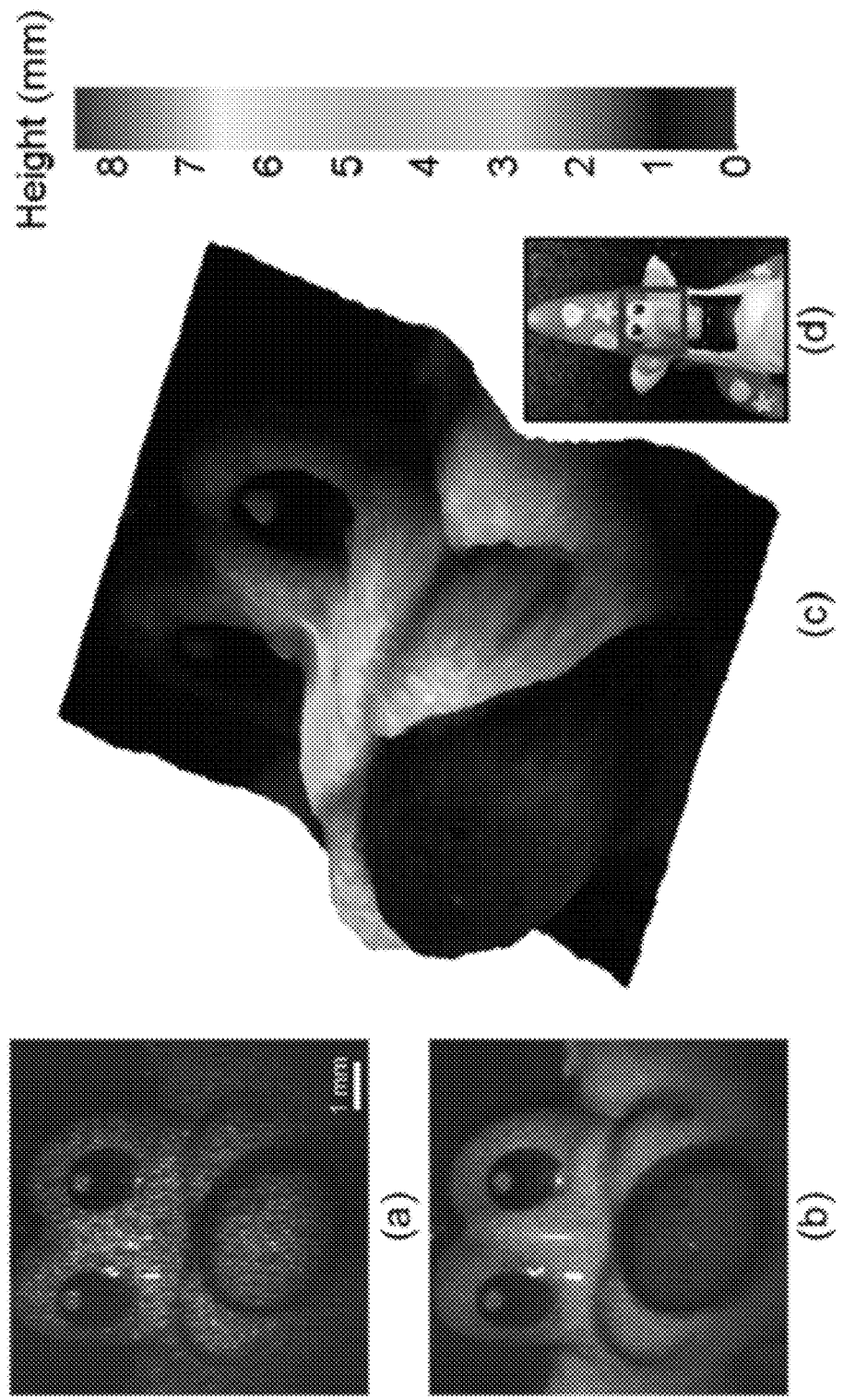
FIGS. 7a to 7d illustrate spectrally encoded imaging using the setup of FIG. 5.

FIG. 7c illustrates a 3D reconstruction obtained from the SM path interferogram scaled with the MM reflectance map. Images obtained from the MM signal have a large depth of field and conserve the same lateral resolution than the SM ones. Indeed, with this exemplary set-up, measured values for depth of field, obtained by translating a mirror were 2.7 mm (theoretical value: 1.7 mm) and 4.9 mm (theoretical value: 5.6 mm) for SM and MM signals respectively. The 10%-90% edge response lateral resolution, measured using a US air force resolution target, was 0.03 mm (theoretical value: 0.02 mm) and 0.03 mm (theoretical value: 0.027 mm) for SM and MM signals respectively. Clinically, this translates into a longer depth of field which allows imaging of samples with a more pronounced height profile, as exemplified in FIGS. 7a-7c.

Figure 8:
FIGS. 8a and 8b illustrate still frames extracted from a video sequence of a wasp's head from detected MM reflectance signals and SM interferogram signals.

To show the full potential of combining reflectance map and interferometric height determination with SEE, we obtained a sequence of 3D profiles of a biological sample. FIGS. 8a and 8b show still frames extracted from a video sequence of a rotating wasp's head obtained from a sequence of 99 simultaneously acquired MM reflectance maps and SM interferometrically determined height profiles. No special sample preparation was required. FIG. 8a is the MM reflectance signal while FIG. 8b is the MM reflectance signal with the height obtained from single mode interferograms. In these acquisitions, the zero difference plane of the interferometer was located at the back of the wasp's head.

For wide-field endoscopy, the DCFC 100 may be used as described above and illustrated in FIG. 1, or the second end 110 may be tapered to provide a given ratio for the inner cladding to core mode field diameter. This ratio may be set to a value that is greater than or equal to about 6.0. In some embodiments, the ratio is set to about 10. In another embodiment, the imaging system of FIG. 4 is used for confocal endomicroscopy. For such an application, the given ratio of inner cladding diameter to core mode diameter is set to a value that is less than or equal to 6. In some embodiments, the ratio is set to about 5.

In order to select the optimal ratio of inner cladding diameter to core mode field diameter, partially coherent imaging systems using Gaussian illumination was explored. We began by examining optical sectioning in partially coherent confocal imaging systems for different detector sizes. A wavelength independent imaging theory can be expressed by defining normalized optical coordinates (u and v) in the axial and radial directions, respectively:

$$u=4kz_s \sin^2(\alpha/2), \qquad (1)$$

and $$v=kr_s \sin(\alpha), \qquad (2)$$

where $k=2\pi/\lambda$, $\lambda$ is the wavelength, $z_s$ and $r_s$ are the axial and radial coordinates at the sample plane and $\alpha$ is the half-angle supported by the objective lens.

Figure 9:
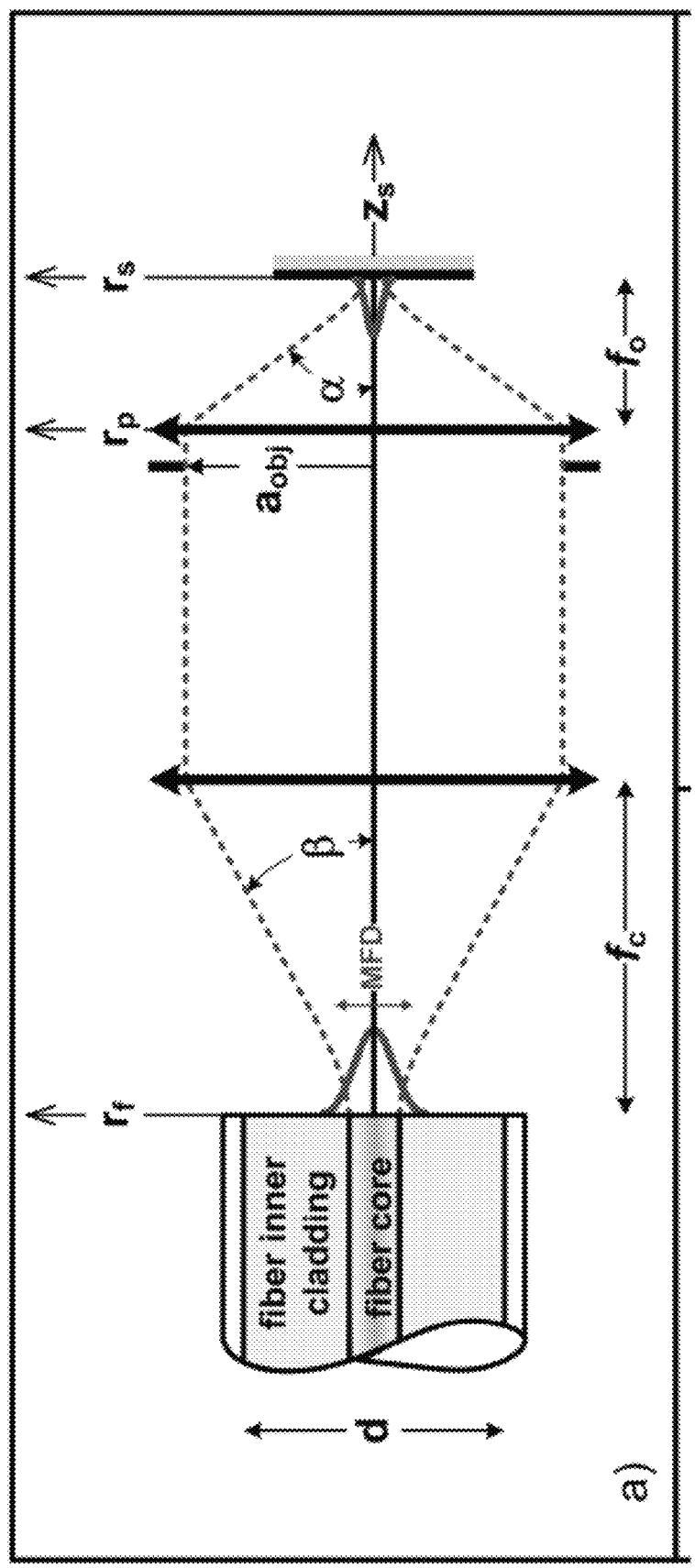
FIG. 9 is a light propagation schematic illustrating confocal imaging with a double clad fiber.

FIG. 9 shows the general configuration for confocal imaging using a DCF. Illumination of the sample comes from the DCF core mode and collection is performed through the inner cladding propagating a large number of orthonormal modes. Because of the orthonormality of the inner cladding modes, confocal imaging using a DCF can be considered as an incoherent sum of multiple coherent detection systems (one for each inner cladding mode). If the number of modes is large enough, the base can be considered complete and imaging can be approximated as being partially coherent. In this partially coherent imaging scheme the intensity measured at the detector's plane (not shown) is given by integrating light reflected back from the sample onto the fiber's plane over the inner cladding collection area. We define the axial plane response of the system as $$I(u) \propto \int_0^{v_p} \left| \int_0^1 P_1(\rho)P_2(\rho)\exp(iu\rho^2)J_0(v\rho)\rho\, d\rho \right|^2 v\, dv \qquad (3)$$

where I(u) is the collected intensity as a function of defocus for different values of $v_p$, the normalized radius of the DCF inner cladding at the plane of the fiber. The equation for $v_p$ is given by $$v_p=k(d/2)\sin(\beta), \qquad (4)$$

where d is the diameter of the DCF's inner cladding and $\beta$ is the reciprocal half-angle at the fiber plane.

$P_{1,2}$ are illumination and collection pupil functions (at the objective plane), respectively, expressed as a function of a normalized radial coordinate ρ, defined as $$\rho = r_p / a_{obj} \quad (5)$$

where $r_p$ is the radial coordinate at the objective lens pupil plane and $a_{obj}$ is the radius of the pupil.

The amplitude of the field at the pupil plane ($P_1(\rho)$) is obtained by examining the illumination pattern. Illumination amplitude, $E_{ill}(r_f)$, from the SM core is function of the radial coordinate $r_f$ (at the fiber plane) and may be approximated by a Gaussian profile:

$$E_{ill}(r_f) = \frac{a_{ill}}{\sqrt{N_f}} \exp\left[-\left(\frac{2r_f}{MFD}\right)^2\right] \quad (6)$$

$a_{ill}$ is the complex amplitude of the fundamental mode. MFD is the mode field diameter which is defined by the diameter at which the intensity drops by a factor $1/e^2$. $N_f$ is a normalization factor given by $$N_f = 2\pi \int_0^\infty \left|\exp\left[-\left(\frac{2r_f}{mfd}\right)^2\right]\right|^2 r_f \, dr_f = \frac{\pi MFD^2}{8} \quad (7)$$

At this point, we define a filling factor A, to take into account the possible under or over filling of the microscope objective pupil as:

$$A = \left(k \frac{a_{obj}}{f_{coll}} \frac{MFD}{2\sqrt{2}}\right)^2 \quad (8)$$

As seen from Eq. (8), the filling factor depends on the MFD (itself a function of the fiber core diameter and numerical aperture) and the focal length of the collimating lens, $f_{coll}$. The amplitude of the Gaussian illumination field falls at $e^{-A/2}$ of its peak value at the edge of the objective lens aperture of radius $a_{obj}$. When the objective lens respects the Abbe condition, the filling factor becomes $$A = \left(kM \sin(\alpha) \frac{MFD}{2\sqrt{2}}\right)^2 \quad (9)$$

Where M is the system's magnification give by $$M = \frac{f_{obj}}{f_{coll}} = \frac{\sin(\beta)}{\sin(\alpha)} \quad (10)$$

Assuming the diameter of the collimating lens is much greater than the beam diameter, we may express the field at the objective lens pupil as $$E_{ill}(r_p) = \frac{a_{ill}}{\sqrt{N_p}} \exp\left[-\left(\frac{r_p \sqrt{A}}{a_{obj}\sqrt{2}}\right)^2\right] \quad (11)$$

where $N_p$ is a normalization factor given by $$N_p = 2\pi \int_0^\infty \left|\exp\left[-\left(\frac{r_p \sqrt{A}}{a_{obj}\sqrt{2}}\right)^2\right]\right|^2 r_p \, dr_p = \frac{n a_{obj}^2}{A}. \quad (12)$$

The expression for the field at the illumination pupil then becomes $$P_1(\rho) = \exp\left[\frac{\rho\sqrt{A}}{\sqrt{2}}\right] \quad (13)$$

The expression for the detection pupil is simply $$P_2(\rho) = 1 \quad (14)$$

The normalized coordinate $v_p$, may thus be rewritten as a function of the ratio d/MFD as $$v_p = \frac{d}{MFD}\sqrt{2A}. \quad (15)$$

Figure 10:
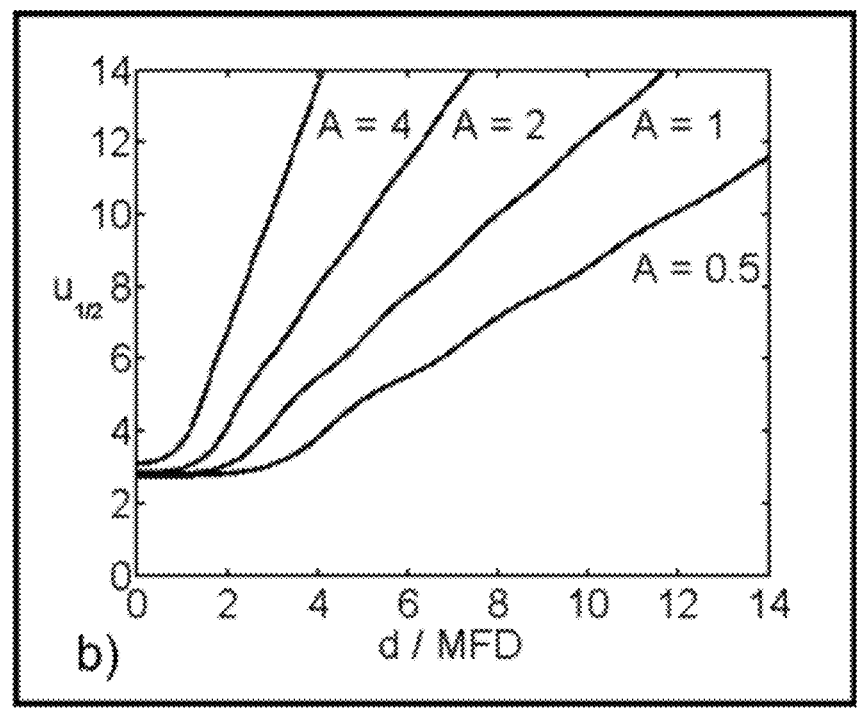
FIG. 10 is a graph showing optical sections for a perfect plane reflector as a function of the ration d/MFD for different values of pupil filling factor A.

We compute I(u) for different values of d/MFD and A. Results are plotted in FIG. 10 and show the value of defocus for which the intensity drops by a factor 2 (i.e. $u_{1/2}$). This development is a crude approximation of a real confocal imaging system with a DCTF, but has the advantage of giving normalized results for any type of DCTF as long as its fundamental mode is nearly Gaussian and the inner cladding is highly MM. It also provides insight on how to optimize a confocal imaging system to balance the signal collection and axial resolution.

Another important criterion to consider in confocal endomicroscopy is light efficiency. Depending on the application, one may wish to favor axial resolution and overfill the objective's pupil (with A≈0.5) or one may favor a more parsimonious use of photons (with A>1) at the expense of a slightly lower resolution. The system's efficiency (defined as the ratio of detected power over input power), η, is function of the illumination ($\eta_1$) and collection ($\eta_2$) efficiencies. The transmitted energy through the objective pupil depends on the filling factor as $$\eta_1 = 1 - e^{-A} \quad (16)$$

For a perfect plane reflector at focus (u=0), the ratio of power detected by a circular detector of radius $v_p$ over the incident power at the detection plane is given by $$n = \frac{\int_0^{v_p} \left|\int_0^1 \exp\left[-\left(\frac{\rho\sqrt{A}}{\sqrt{2}}\right)^2\right] I_0(v\rho)\rho \, d\rho\right|^2 v \, dv}{\int_0^\infty \left|\int_0^1 \exp\left[-\left(\frac{\rho\sqrt{A}}{\sqrt{2}}\right)^2\right] I_0(v\rho)\rho \, d\rho\right|^2 v \, dv} \quad (17)$$

Under these conditions, the system's efficiency is simply given by $$\eta = \eta_1 \eta_2 \quad (18)$$

Figure 11:
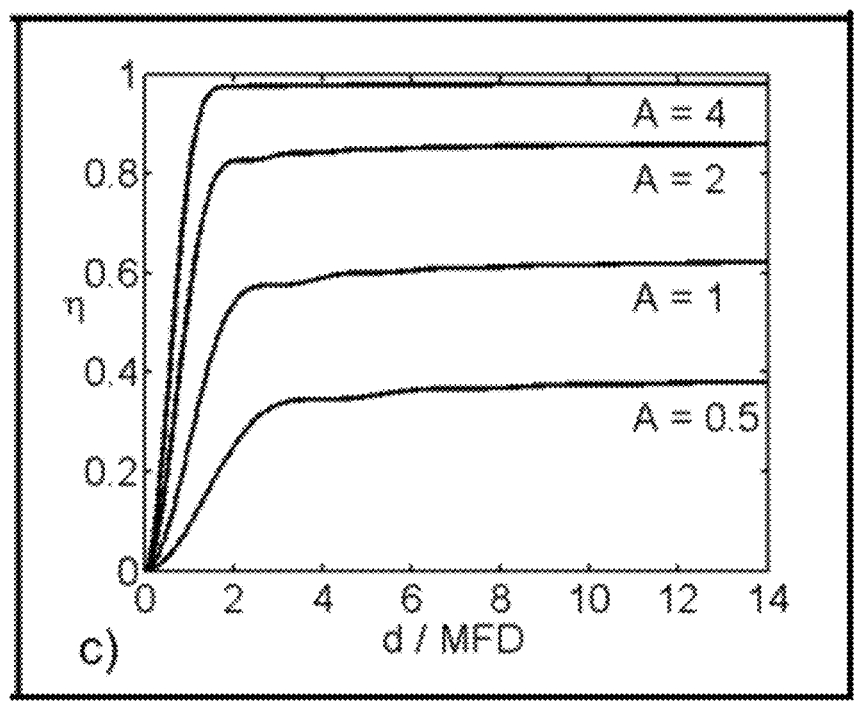
FIG. 11 is a graph showing excitation efficiency for a perfect plane reflector at focus as a function of the ration d/MFD for different values of pupil filling factor A.

FIG. 11 shows η for different values of ratio d/MFD and various filling factors A. For a perfect planar reflector at focus, η rapidly stabilizes around its maximal value for d/MFD ratios larger than 2, but, in most in vivo biomedical applications, the sample is a bulk diffusive medium incorporating optically smooth reflective surfaces. In this type of sample, η will continue to grow for ratios d/MFD larger than 2 because of out-of-plane diffused and reflected signals.

Another roadblock for the use of single fiber endomicroscopy in the clinical world is speckle contrast. Speckle noise creates patterns in the images that can be misinterpreted by clinicians. When light is reflected by a diffusing sample, a speckle pattern is formed at the fiber plane. If an SM fiber is used for illumination and collection, the speckle pattern will excite the fundamental mode of the fiber following a Gaussian probability function in amplitude. The intensity image formed by scanning the diffusive sample will then have a speckle contrast of 1. If an MM fiber (or the inner cladding of a DCTF) is used for the detection, each orthogonal mode will independently be excited by the speckle pattern following a Gaussian probability function in amplitude. The mean intensity of each orthogonal mode will depend on the speckle pattern's coherence area $A_c$ at the fiber plane and on the mode's profile. If the detector at the end of the fiber is larger than the field coming from the fiber, each mode will be detected independently and the resulting intensity image will have a lower speckle contrast. In this case, the speckle contrast $C_{MM}$ is given by:

$$C_{MM} = \frac{\sigma_s}{\bar{I}_s} = \frac{\sqrt{\sum_{n=1}^{N} \bar{I}_s^2}}{\sum_{n=1}^{N} \bar{I}_n} \quad (19)$$

where $\sigma_s$ is the standard deviation of the detected intensity, $\bar{I}_s$ is the mean of the detected intensity, N is the number of modes and $\bar{I}_n$ is the mean of the intensity coupled in mode n of the inner cladding.

Another way to explain the reduction in the speckle contrast is to consider the set of orthogonal modes to be complete (highly MM fiber). With this approximation, the imaging becomes again partially coherent and the highly MM fiber can be approximated by a circular detector sensitive to the intensity of the field at the fiber plane of diameter d. In this case, we are in the presence of an integrated speckle statistic. For a circular detector of perfect intensity sensitivity of 1 and area $A_d$, in the approximation that $A_d \gg A$, the speckle contrast $C_d$ is given by:

$$C_d \approx \sqrt{\frac{A_c}{A_d}} \quad (20)$$

So, if the speckle spot size at the detection plane is smaller than the detection area, with a larger detection diameter d the speckle pattern will be integrated over a larger area and the speckle contrast will be reduced drastically.

Figure 12:
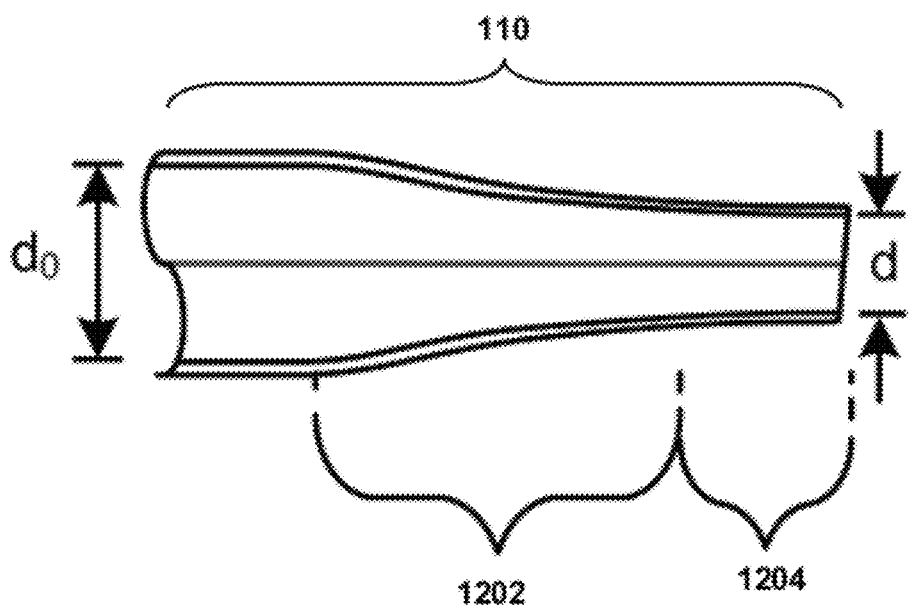
FIG. 12 is a schematic illustration of a tapered second end of the coupler of FIG. 1.

FIG. 12 is an exemplary embodiment showing the second end 110 as a tapered end, including a transition section 1202 and a constant section 1204. At the constant section 1204, the ratio of the inner cladding to the core mode field diameter is set to a value ranging from about 0.1 to about 6.0 for confocal endomicroscopy and greater than or equal to about 6.0 for wide-field endoscopy. In one embodiment, the tapered end is provided by applying known tapering techniques, as described above, to the second end 110 of the DCFC 100.

In an alternative embodiment, a double-clad fiber having the desired dimensions and properties is spliced to the second end 110 of the DCFC 100 from FIG. 1. Also alternatively, a double-clad fiber segment may be tapered in order to obtain the desired dimensions and properties, and then spliced to the second end 110 of the DCFC 100. Tapered fibers may be fabricated such that the evolution of the core mode is adiabatic, i.e. there is no coupling of the fundamental core mode to higher-order modes. This ensures that SM illumination is lossless and achromatic, allowing implementations of spectral encoding and interferometric imaging. In one embodiment, the double-clad tapered fiber is a silica glass commercial fiber. The core is germanium doped, with a numerical aperture of 0.12, a diameter of 9 µm, and a cutoff wavelength of 1250 nm. The inner cladding is pure silica, with a numerical aperture of 0.20 and a diameter of 105 µm. The outer cladding is fluorine-doped and has a diameter of 125 µm.

Figure 13:
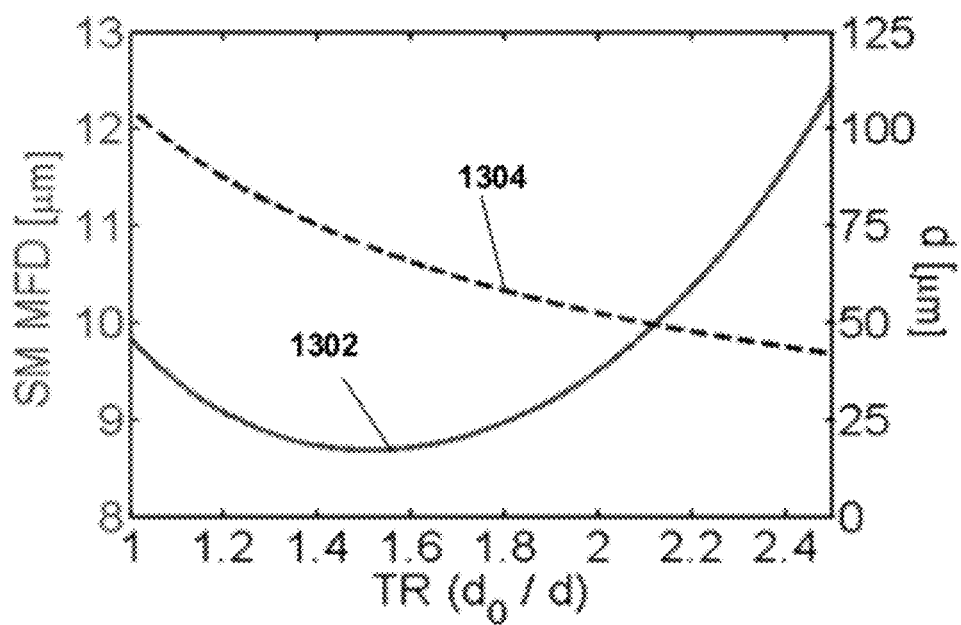
FIG. 13 is a graph showing MFD and inner cladding diameter as a function of the taper ratio.

FIG. 13 shows the evolution of the SM illumination beam core mode field diameter (MFD) 1302 and the MM inner cladding diameter d 1304 when a DCF is tapered as a function of the taper ratio (TR) defined as the reduction factor $d_0/d$, larger values representing larger reductions. The MFD of the fundamental mode 1302 initially decreases with higher TR but eventually increases as the mode diffracts out of the smaller core. As TR varies from 1 to 2.5, the core mode MFD 1302 has a minimal value of 9 µm and increases up to 12 µm. The MM inner cladding collection diameter 1304, however, decreases as TR increases following an inversely proportional law. A wide range of MM detection diameter over SM illumination ratios are thus obtainable as TR is varied during the tapering.

Fabrication and characterization of the DCTF may be obtained using a setup similar to what was described above for fabricating the DCFC 100. Fabrication starts by splicing a DCF with two SM fibers connected with the broadband source and the optical spectrum analyzer. The two splices ensure that only the transmission in the core mode is characterized. Then, the fiber is stripped over the length to be tapered and cleaned with acetone. After the final inspection of the fiber with the microscope, the tapering process starts. The adiabaticity criterion is met by using a traveling flame which travels over a course of 8 mm during the tapering of the DCF. When the fiber reaches a TR of 2 the tapering is stopped. The fiber is angled cleaved at the center of the taper and inspected on a splicing station. This inspection allows us to measure the final TR of the DCFT by comparison with the original cross-section of the DCF and the quality of the angled cleave.

An angled cleave of about 4.0° to about 12.0°, with an exemplary value of 7.2°, prevents the illumination light to be backreflected into the core mode. Most of the backreflected light couples into the outer cladding modes. These outer cladding backreflections are attenuated by using a higher index gel drop in the constant section 1204 of the DCTF.

Figure 14:
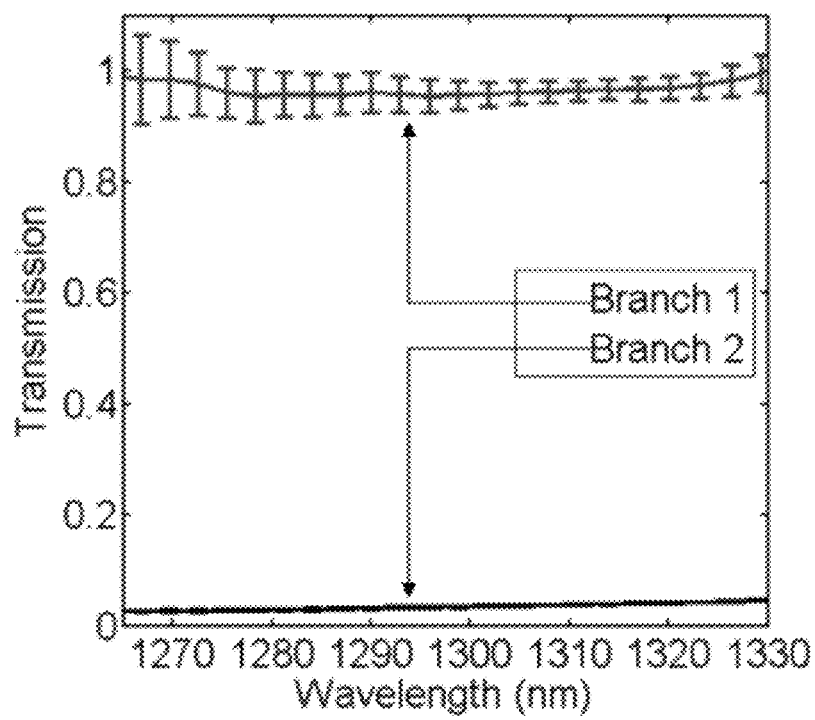
FIG. 14 is a graph illustrating a spectral response of the SM core transmission for the coupler of FIG. 1 with tapered second end.
Figure 15:
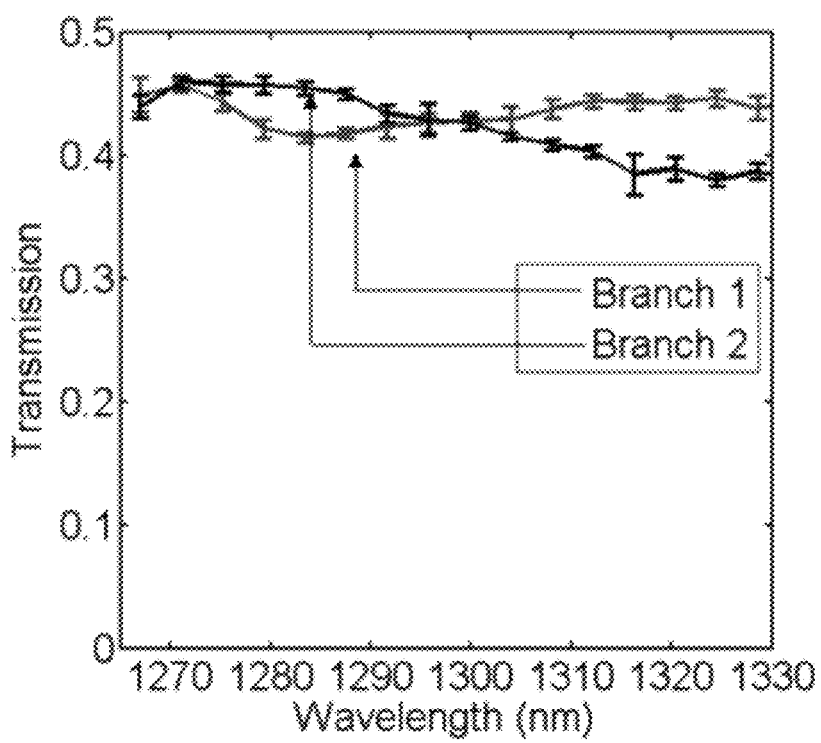
FIG. 15 is a graph illustrating a spectral response of the MM inner cladding transmission for the coupler of FIG. 1 with tapered second end.

After the SM spectral characterization and the inspection of the cleave of the DCTF, the DCTF is spliced with the DCFC 100. The spectral characterization of the SM transmission of the DCFC with its tapered second end 110 is done by multiplying the SM spectral response of the DCTF with the SM spectral response of the DCFC, and is illustrated in FIG. 14. The spectral characterization of the MM transmission of the DCFC with its tapered second end 110 is done by using a wavelength-swept source and a diffuser, and is illustrated in FIG. 15. The diffuser allows the excitation of the lower and higher order modes of the tapered second end 110 and the wavelength-swept source allows the characterization of the transmission of the entire device with a photo-detector large enough to collect all of the light at the output.

Figure 16:
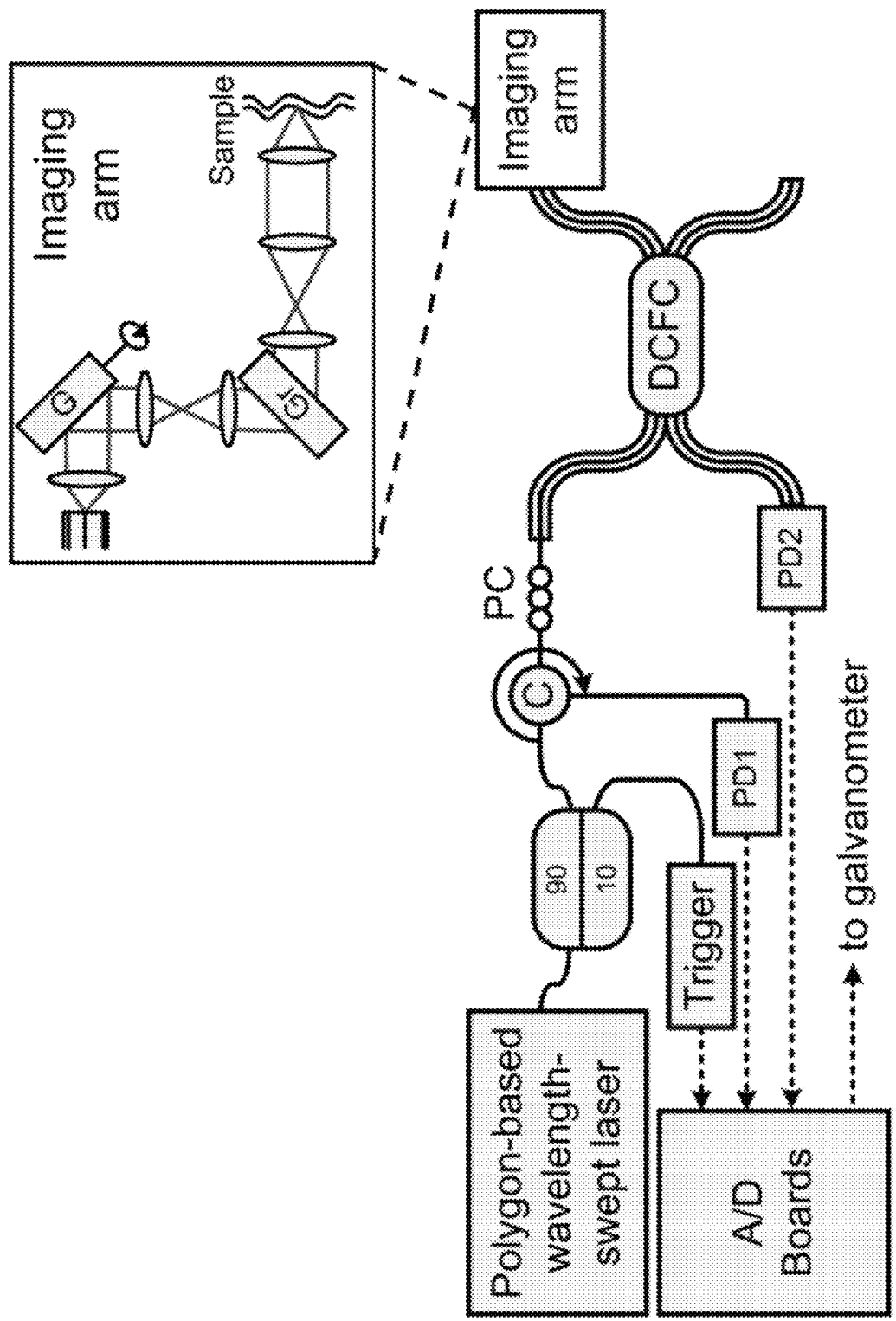
FIG. 16 is an exemplary setup used to test the coupler of FIG. 1 for confocal endomicroscopy.

FIG. 16 illustrates the setup used to test the DCFC 100 with tapered second end 110 for confocal imaging. The imaging setup consists of a polygon based wavelength-swept laser ($\lambda_0$=1310 nm, $\Delta\lambda$=80 nm, sweep rate=8.9 kHz) coupled to the core of the DCFC for illumination of the sample through a standard SE imaging arm. The SM output of the laser is spliced to an SM fiber circulator itself spliced to the SM core of the DCFC for quasi lossless illumination of the sample. SE confocal imaging is achieved by using a galvanometer-mounted mirror for the slow axis scan (Cambridge Technology, Lexington, Mass.) and a holographic transmission grating (Wasatch Photonics, Logan, Utah, 1125 lines/mm) for the fast axis. A high NA microscope objective ((Olympus, Tokyo, Japan, LUMFLN 60XW, NA=1) is used to illuminate and collect light from the sample. A pupil filling factor of A=1.2 was obtained by enlarging the collimated beam ($f_{collimator}$=11 mm, Thorlabs, Newtown, N.J., C220THE-C) beam through a telecentric telescope made from two achromatic lenses ($f_1$=50 mm and $f_2$=150 mm, Edmund, Barrington, N.J., NT45-803 and NT47-380) arranged in a 4-f configuration. Coherent light backscattered from the sample is collected by the core of the DCTF and sent to an InGaAs photo-detector (New Focus, 2117-FC) through the circulator. Diffuse backscattered light is collected by the inner cladding of the DCTF and sent via the second branch of the DCFC to another identical photo-detector (light sent to the first branch is lost at the splice between the DCFC and the SM fiber leading to the circulator). A rapid digitizer simultaneously acquires single- and multi-mode signals for comparison. The galvanometer is controlled by a separate ND board.

The axial resolution was measured by using a mirror mounted on a piezo-electric translation stage (Burleigh, PCS-5000). The axial 50:50 plane response for the SM signal is 3.4±0.1 mm comparatively to 1.3 mm for a SM fiber based confocal microscope with a filling factor A of 1.2. The axial 50:50 plane response for the MM signal is 5.8±0.1 mm comparatively to 4 mm for a partially coherent SM confocal microscope with a filling factor A of 1.2 and a d/MFD ratio of 5.5. The lateral resolution was measured by using a resolution target (Edmund, Barrington, N.J., U.S. Airforce 1951). The 90:10 edge response for the SM signal is 0.76±0.03 mm comparatively to 0.6 for a perfect confocal microscope while the 90:10 edge response for the MM signal is 1.18±0.04 mm. The difference between the theoretical and experimental value for the axial and lateral resolutions may be explained by the use of the scalar paraxial approximation, the use of an objective designed for wavelengths in the visible part of the spectrum and/or because of the different aberrations.

Figure 17:
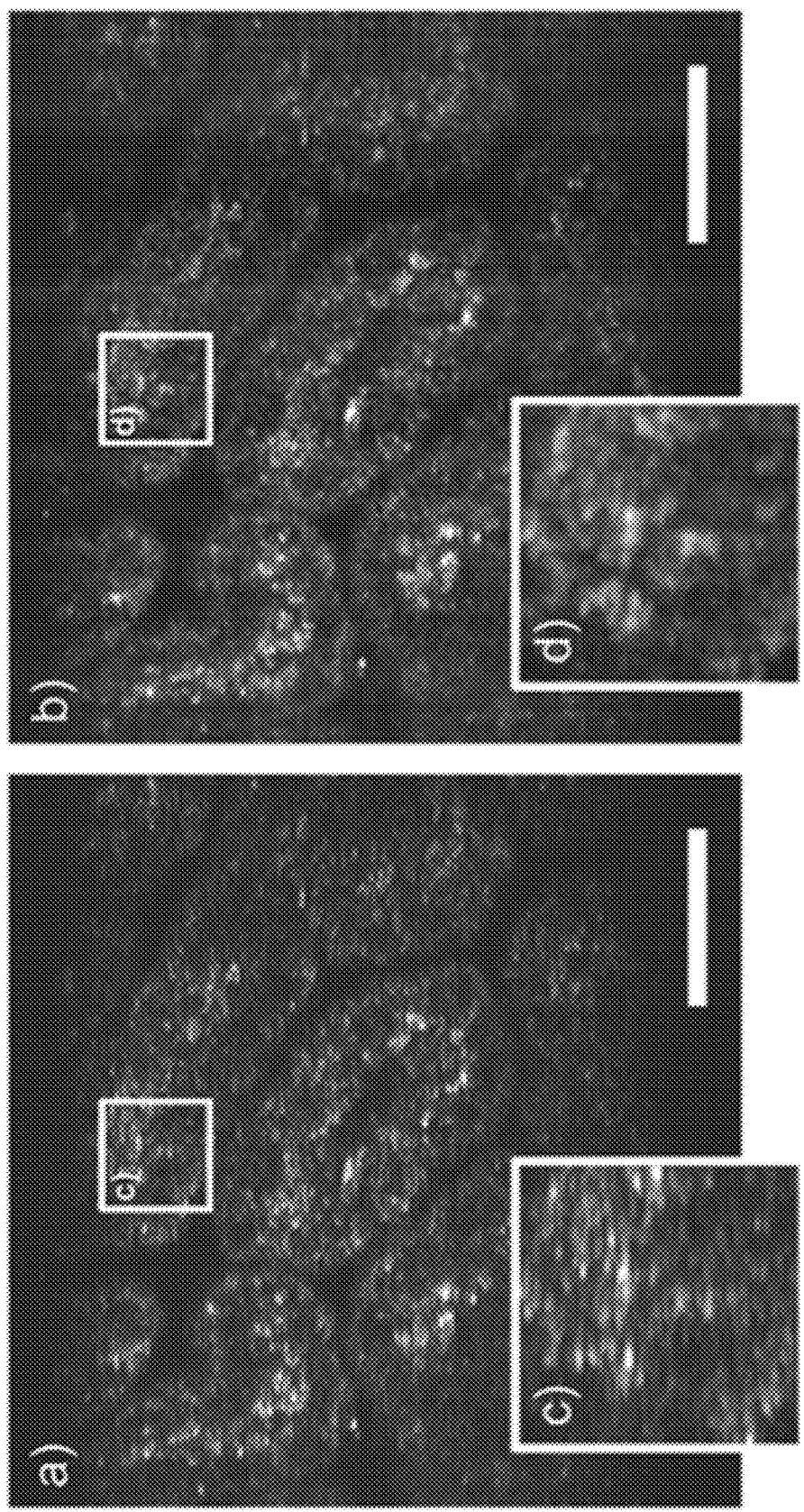
FIGS. 17a-17d are acquired images of a seven day old mouse embryo for the SM signal and the MM signal using the setup of FIG. 16.

To show the potential of the DCTF for confocal imaging of biological samples we imaged a seven day old mouse embryo fixed in a solution of 4% of paraformaldeide. FIG. 17a is a twenty frames average of the SM signal and FIG. 17b is a twenty frames average of the MM signal. SM and MM 1024×1024 images were acquired simultaneously at 10 MHz resulting in a 8.8 fps imaging for each signal. Zooming in the same region of the SM and MM images (see FIGS. 17c and 17d), allows visualization of speckle reduction on three round structures in the MM signal not seen in the SM image because of the higher speckle contrast. The vertical bands visible on FIG. 17b reflects a slight achromaticity of the DCFC that would not affect piezo-based single fiber confocal endomicroscopes.

Therefore, the DCFC 100 has been shown to be useful in many single-fiber endoscopes. This all-fiber technology allows excitation and collection via the SM core of the fiber with negligible loss and collection of >42% of the multiply scattered light collected by the inner-cladding to the detection branch of the coupler. Moreover, the DCFC 100 may be produced by fusing and tapering commercially available DCF in a manner that is compatible with industry standards to fabricate this device reproducibly and at low cost. Furthermore, the design may be adapted for the application of a passive all-fiber device for confocal endomicroscopy (from 1265 nm to 1325 nm). This device allows an SM illumination on the sample and simultaneous SM and MM detection. The tapered second end 110 of the DCFC 100 allows d/MFD ratios varying from 5 to 10. This flexibility of the different illumination and collection schemes allows many compromises between the optical sectioning, the collected intensity and the speckle contrast.

It should be noted that the imaging modules provided in the various setups and systems may be adapted to perform various image processing functions using known image processing devices, such as any device that can perform operations on data. Examples are a central processing unit (CPU), a front-end processor, a microprocessor, a graphics processing unit (GPU/VPU), a physics processing unit (PPU), a digital signal processor, and a network processor. Applications may be coupled to the processor and configured to perform various tasks as explained above. The embodiments of the invention described above are intended to be exemplary only. The scope of the invention is therefore intended to be limited solely by the scope of the appended claims.

The invention claimed is:

1. A double-clad fiber coupler comprising:
    a first double-clad fiber having a first end, a second end, and a first middle portion therebetween, and having a first core, a first inner cladding, and a first outer cladding;
    a second double-clad fiber having a third end, a fourth end, and a second middle portion therebetween and having a second core, a second inner cladding, and a second outer cladding; and
    a fused region composed of the first middle portion fused to the second middle portion, wherein the first core and the second core remain separate and the first inner cladding and the second inner cladding are coupled to form a fused inner cladding, the fused region comprising a first diameter transition section, a constant diameter section, and a second diameter transition section, the first diameter transition section corresponding to a down-taper of the fused region and the second diameter transition section corresponding to an up-taper of the fused region, the fused region section having a predetermined taper ratio, and wherein the fused region allows light injected in the first core at the first end to be transmitted in the first core to the second end, light injected in the first core at the second end is transmitted in the first core to the first end, and light injected in the first inner cladding at the second end is substantially equally split between the first inner cladding towards the first end and the second inner cladding towards the third end;
wherein the predetermined taper ratio is comprised between about 0.1 and about 0.6.

2. A double-clad fiber coupler comprising:
    a first double-clad fiber having a first end, a second end, and a first middle portion therebetween, and having a first core, a first inner cladding, and a first outer cladding;
    a second double-clad fiber having a third end, a fourth end, and a second middle portion therebetween and having a second core, a second inner cladding, and a second outer cladding; and
    a fused region composed of the first middle portion fused to the second middle portion, wherein the first core and the second core remain separate and the first inner cladding and the second inner cladding are coupled to form a fused inner cladding, the fused region comprising a first diameter transition section, a constant diameter section, and a second diameter transition section, the first diameter transition section corresponding to a down-taper of the fused region and the second diameter transition section corresponding to an up-taper of the fused region, the fused region section having a predetermined taper ratio, and wherein the fused region allows light injected in the first core at the first end to be transmitted in the first core to the second end, light injected in the first core at the second end is transmitted in the first core to the first end, and light injected in the first inner cladding at the second end is substantially equally split between the first inner cladding towards the first end and the second inner cladding towards the third end;

wherein at least one of the first double-clad fiber and the second double clad fiber have core mode field, inner cladding, and outer cladding diameters of about 9.0 µm, about 105 µm, and about 125 µm, respectively, at the first end and third end, respectively.

3. A double-clad fiber coupler comprising:
a first double-clad fiber having a first end, a second end, and a first middle portion therebetween, and having a first core, a first inner cladding, and a first outer cladding;
a second double-clad fiber having a third end, a fourth end, and a second middle portion therebetween and having a second core, a second inner cladding, and a second outer cladding; and
a fused region composed of the first middle portion fused to the second middle portion, wherein the first core and the second core remain separate and the first inner cladding and the second inner cladding are coupled to form a fused inner cladding, the fused region comprising a first diameter transition section, a constant diameter section, and a second diameter transition section, the first diameter transition section corresponding to a down-taper of the fused region and the second diameter transition section corresponding to an up-taper of the fused region, the fused region section having a predetermined taper ratio, and wherein the fused region allows light injected in the first core at the first end to be transmitted in the first core to the second end, light injected in the first core at the second end is transmitted in the first core to the first end, and light injected in the first inner cladding at the second end is substantially equally split between the first inner cladding towards the first end and the second inner cladding towards the third end;
wherein the second end of the first double-clad fiber is tapered in order to obtain a given ratio of a first inner cladding diameter to a first core mode field diameter.

4. The fiber coupler of claim 3, wherein the given ratio is greater than or equal to about 6.0.

5. The fiber coupler of claim 3, wherein the given ratio is less than or equal to about 6.0.

6. The fiber coupler of claim 5, wherein the first core mode field diameter, the first inner cladding diameter, and a first outer cladding diameter are about 9.5 µm, about 52.5 µm, and about 62.5 µm, respectively, at the tapered second end.

7. The fiber coupler of claim 5, wherein the tapered second end is cleaved at an angle between about 4.0 and about 12.0 degrees in order to prevent backscattering of illumination light into the first core.

8. The fiber coupler of claim 7, wherein the tapered second end is surrounded by an index-matching material in order to dissipate illumination light backscattered by the second end cleaved at an angle and to prevent said light from propagating back to the second end of the fiber coupler.

9. A double-clad fiber imaging system comprising:
a laser source for generating a light signal;
a single mode fiber operatively connected to an output of the laser source for receiving and propagating the light signal;
a double-clad fiber coupler operatively connected to the single mode fiber for receiving the light signal, the double-clad fiber coupler comprising:
a first double-clad fiber having a first end, a second end, and a first middle portion therebetween, and having a first core, a first inner cladding, and a first outer cladding;
a second double-clad fiber having a third end, a fourth end, and a second middle portion therebetween and having a second core, a second inner cladding, and a second outer cladding; and
a fused region composed of the first middle portion fused to the second middle portion, wherein the first core and the second core remain separate and the first inner cladding and the second inner cladding are coupled to form a fused inner cladding, the fused region comprising a first diameter transition section, a constant diameter section, and a second diameter transition section, the first diameter transition section corresponding to a down-taper of the fused region and the second diameter transition section corresponding to an up-taper of the fused region, the fused region section having a predetermined taper ratio, and wherein the fused region allows light injected in the first core at the first end to be transmitted in the first core to the second end, light injected in the first core at the second end is transmitted in the first core to the first end, and light injected in the first inner cladding at the second end is substantially equally split between the first inner cladding towards the first end and the second inner cladding towards the third end;
an imaging module operatively connected to the second end of the first double-clad fiber and adapted for receiving coherent light propagating from the first end of the first double-clad fiber to the second end and for sending backscattered coherent and diffuse light back to the second end;
a first photo-detector operatively connected to the third end of the second double-clad fiber for collecting backscattered diffuse light propagating from the second end of the second double-clad fiber to the third end; and
a second photo-detector operatively connected to the first end of the first double clad fiber for collecting backscattered coherent light propagating from the second end of the first double-clad fiber to the first end;
wherein the predetermined taper ratio is between about 0.1 and about 0.6.

10. A double-clad fiber imaging system comprising:
a laser source for generating a light signal;
a single mode fiber operatively connected to an output of the laser source for receiving and propagating the light signal:
a double-clad fiber coupler operatively connected to the single mode fiber for receiving the light signal, the double-clad fiber coupler comprising:
a first double-clad fiber having a first end, a second end, and a first middle portion therebetween, and having a first core, a first inner cladding, and a first outer cladding;
a second double-clad fiber having a third end, a fourth end, and a second middle portion therebetween and having a second core, a second inner cladding, and a second outer cladding; and a fused region composed of the first middle portion fused to the second middle portion, wherein the first core and the second core remain separate and the first inner cladding and the second inner cladding are coupled to form a fused inner cladding, the fused region comprising a first diameter transition section, a constant diameter section, and a second diameter transition section, the first diameter transition section corresponding to a down-taper of the fused region and the second diameter transition section corresponding to an up-taper of the fused region, the fused region section having a predetermined taper ratio, and wherein the fused region allows light injected in the first core at the first end to be transmitted in the first core to the second end, light injected in the first core at the second end is transmitted in the first core to the first end, and light injected in the first inner cladding at the second end is substantially equally split between the first inner cladding towards the first end and the second inner cladding towards the third end;

an imaging module operatively connected to the second end of the first double-clad fiber and adapted for receiving coherent light propagating from the first end of the first double-clad fiber to the second end and for sending backscattered coherent and diffuse light back to the second end;

a first photo-detector operatively connected to the third end of the second double-clad fiber for collecting backscattered diffuse light propagating from the second end of the second double-clad fiber to the third end; and a second photo-detector operatively connected to the first end of the first double clad fiber for collecting backscattered coherent light propagating from the second end of the first double-clad fiber to the first end;

wherein the second end of the first double-clad fiber is tapered in order to obtain a given ratio of a first inner cladding diameter to a first core mode field diameter.

11. The system of claim 10, wherein the given ratio is greater than or equal to about 6.0, and the imaging system is a wide-field endoscopy system.

12. The system of claim 11, wherein the imaging module performs spectral encoding and comprises a collimating lens, a galvanometer mounted mirror, a transmission grating, and a focusing lens.

13. The system of claim 12, further comprising a polarization controller to optimize transmission through the transmission grating.

14. The system of claim 11, wherein the imaging module comprises an image processing device for superposing low-speckle multi-mode reflectance data with single-mode height data to generate images emulating stereoscopic vision.

15. The system of claim 10, wherein the given ratio is less than or equal to about 6.0, and the imaging system is a confocal endomicroscopy system.

16. The system of claim 15, wherein the imaging module performs spectral encoding and comprises a galvanometer-mounted mirror for slow axis scan and a holographic transmission grating for fast axis scan.

17. The system of claim 16, wherein the imaging module comprises a microscope objective to illuminate and collect light.

18. The system of claim 15, wherein the imaging module comprises an image processing device adapted for micrometric resolution and optical sectioning of images.

19. The system of claim 18, wherein the imaging module is adapted to perform the optical sectioning through spatial filtering of remitted light.

* * * * *